(12) United States Patent
Shin et al.

(10) Patent No.: US 9,913,657 B2
(45) Date of Patent: Mar. 13, 2018

(54) APPARATUS FOR TRANSLUMINAL PROCEDURES

(71) Applicants: TAEWOONG MEDICAL CO., LTD, Gyeonggi-do (KR); Kyong Min Shin, Seoul (KR)

(72) Inventors: Kyong Min Shin, Seoul (KR); Yong Hyun Won, Gyoenggi-do (KR)

(73) Assignees: TAEWOONG MEDICAL CO., LTD, Gyeonggi-do (KR); Kyong Min Shin, Seoul (KR)

( * ) Notice: Subject to any disclaimer, the term of this patent is extended or adjusted under 35 U.S.C. 154(b) by 0 days.

(21) Appl. No.: 14/758,453

(22) PCT Filed: Dec. 3, 2013

(86) PCT No.: PCT/KR2013/011095
§ 371 (c)(1),
(2) Date: Jun. 29, 2015

(87) PCT Pub. No.: WO2015/072614
PCT Pub. Date: May 21, 2015

(65) Prior Publication Data
US 2016/0242803 A1    Aug. 25, 2016

(30) Foreign Application Priority Data

Nov. 14, 2013  (KR) .................. 10-2013-0138505

(51) Int. Cl.
*A61B 17/32*    (2006.01)
*A61B 17/3205*   (2006.01)
(Continued)

(52) U.S. Cl.
CPC .. *A61B 17/32056* (2013.01); *A61B 17/22031* (2013.01); *A61B 17/29* (2013.01);
(Continued)

(58) Field of Classification Search
CPC ........ A61B 17/32056; A61B 17/22031; A61B 17/29; A61B 17/2909; A61B 2017/00269;
(Continued)

(56) References Cited

U.S. PATENT DOCUMENTS

2001/0051822 A1   12/2001  Stack et al.
2006/0116689 A1*   6/2006  Albans ............... A61B 17/1617
                                                      606/92

(Continued)

FOREIGN PATENT DOCUMENTS

KR         101109734         2/2012
WO    WO 2009/140212        11/2009

*Primary Examiner* — Tuan V Nguyen
(74) *Attorney, Agent, or Firm* — IP & T Group LLP

(57) ABSTRACT

An apparatus for a transluminal procedure includes: a case composed of a front case part formed in the shape of a pipe and having a locking groove at a rear end, a central case part combined with the front case part and having a button hole at a rear end, and a rear case part combined with the central case part and having a through-hole formed ahead of a button groove coming in contact with the button hole at a center; a locking member having a button and a locking end; an operation member formed in the shape of a pipe and moving up and down in the case; an inner wire in live operation member and locked to the case; and an outer tube fitted on the inner wire and fixed ahead of the operation member.

21 Claims, 14 Drawing Sheets

(51) Int. Cl.
  *A61B 17/29* (2006.01)
  *A61B 17/00* (2006.01)
  *A61B 17/22* (2006.01)

(52) U.S. Cl.
  CPC .............. *A61B 17/2909* (2013.01); *A61B 2017/00269* (2013.01); *A61B 2017/22069* (2013.01); *A61B 2017/2919* (2013.01); *A61B 2017/2946* (2013.01)

(58) Field of Classification Search
  CPC .. A61B 2017/22069; A61B 2017/2919; A61B 2017/2946
  See application file for complete search history.

(56) References Cited

U.S. PATENT DOCUMENTS

2007/0239252 A1    10/2007    Hopkins et al.
2013/0226308 A1    8/2013    Gerdts et al.

* cited by examiner

APPARATUS FOR TRANSLUMINAL PROCEDURES

This application is a national stage application of PCT/KR2013/011095 filed on Dec. 3, 2013, which claims priority of Korean patent application number 10-2013-0138505 filed on Nov. 14, 2013. The disclosure of each of the foregoing applications is incorporated herein by reference in its entirety.

TECHNICAL FIELD

The present invention relates to an apparatus for a transluminal procedure, particularly, to an apparatus for a transluminal procedure that can be simply moved to adjust the position because a plastic stent can be fixed by pressing and that can automatically return, thereby allowing an operator to more conveniently perform a procedure in use.

BACKGROUND ART

In general, stricture of organs or blood vessels may be caused and internal secreting fluid cannot smoothly flow due to a disease in a human body and operations, and several parts of a human body cannot normally work due to stricture of organs and blood vessels.

When internal secreting fluid cannot smoothly flow, various kinds of plastic stents are used, and particularly, when stricture of the bile duct and ERBD (Endoscopic retrograde Biliary Drainage) occurs, an operator inserts a plastic stent through an endoscope so that bile and secretion are smoothly discharged.

Further, ERCP (Endoscopic retrograde cholangiopancreatography) is an examination that inserts an endoscope into the duodenum and examines diseased parts of the bile duct and the pancreatic duct through a small hole called the ampulla of Vater. However, the ampulla that is cut by a knife called Sphinctenotome through EST (endoscopic sphincterectomy) after an endoscope is inserted for examining the bile duct and the pancreatic duct may be inflamed or may be in danger of secondary complications (cholangitis or pancreatitis).

A procedure of inserting a plastic stent is performed to prevent such secondary complications.

There are various kinds of plastic stents, including the shapes in which both ends are rolled in the same direction or different directions or barbs are formed at both ends in accordance with the usage or the procedure places, and the bodies are cylindrical in most cases.

According to the common way of the related art that inserts a plastic stent into a body for a procedure, a double pipe of a guide catheter and a push pipe moving forward/backward along the guide catheter is used, in which a plastic stent is fitted in the guide catheter partially exposed and inserted into a lumen and then the push pipe is moved forward to operate on a desired portion.

An operation tool such as specific forceps, which pushes or pulls the plastic stent, is used to adjust, the position of the plastic stent.

However, when a guide catheter is used, its size should be changed in accordance with the kind or size of a plastic stent and it is difficult to adjust the position after an operation.

In order to solve this problem, a way of coupling a plastic stent to the front of a guide catheter with a suture, inserting the stent into a lumen of a body and moving the guide catheter to the accurate operation position, and then separating the plastic stent from the guide catheter by untying the suture has recently been proposed.

However, this operation type of coupling a plastic stent to a guide catheter with a suture can ensure stability because the guide catheter and the plastic stent are coupled in a single unit, but there is a problem in that it is required to untie the suture to perform an operation and readjust the position of the plastic stent after removing the suture.

There is a strong need of an operation tool that can adjust the position for an operation of a plastic stent, adjust the position after the operation, remove a portion of a tissue like forceps, and excise a tissue like a snare, using an operation mechanism moving forward/backward.

DISCLOSURE

Technical Problem

An object of the present invention is to provide an apparatus for a transluminal procedure that can fix and move a plastic stent and adjust the position of the plastic stent by coming in contact with the inner side of the plastic stent by simple pressing.

Another object of the present invention is to adjust the increase in diameter of a variable portion in multi-step locking by pressing and to return it to the initial position with an elastic force in unlocking.

Another object of the present invention is to simplify repair and replace components by separately making them for different functions

Technical Solution

In order to achieve the object, the present invention provides an apparatus for a transluminal procedure, in which a case is composed of a front case part formed in the shape of a pipe and having a locking groove at a rear end, a central case part combined with the front case part and having a button hole at a rear end, and a rear case part combined with the central case part and having a through-hole formed ahead of a button groove coming in contact with the button hole at a center, a button protrudes rearward from a locking end inserted in the through-hole, the button is supported by an elastic member disposed in the button groove of the rear case part, returns after being pressed, and constitutes a locking member having the locking end, an operation member is formed in the shape of a pipe and moves up and down in the case, an inner wire is inserted in the operation member and locked to the case, and an outer tube is fitted on the inner wire and fixed ahead of the operation member.

Advantageous Effects

According to the present invention, it is possible to fix and move a plastic stent and adjust the position of the plastic stent by coming in close contact with the inner side of the plastic sent by simple pressing, so it allows for a convenient operation.

Further, it is possible to adjust the amount of increase in diameter of the variable portion under pressure in multi-stage operation and to return the variable portion by an elastic force in unlocking, so it is possible to allow repeated operations and not increase fatigue of an operator.

Further, the components are separately made to perform different functions, so they can be simply repaired and replaced, so the maintenance cost is reduced.

Figure 1:
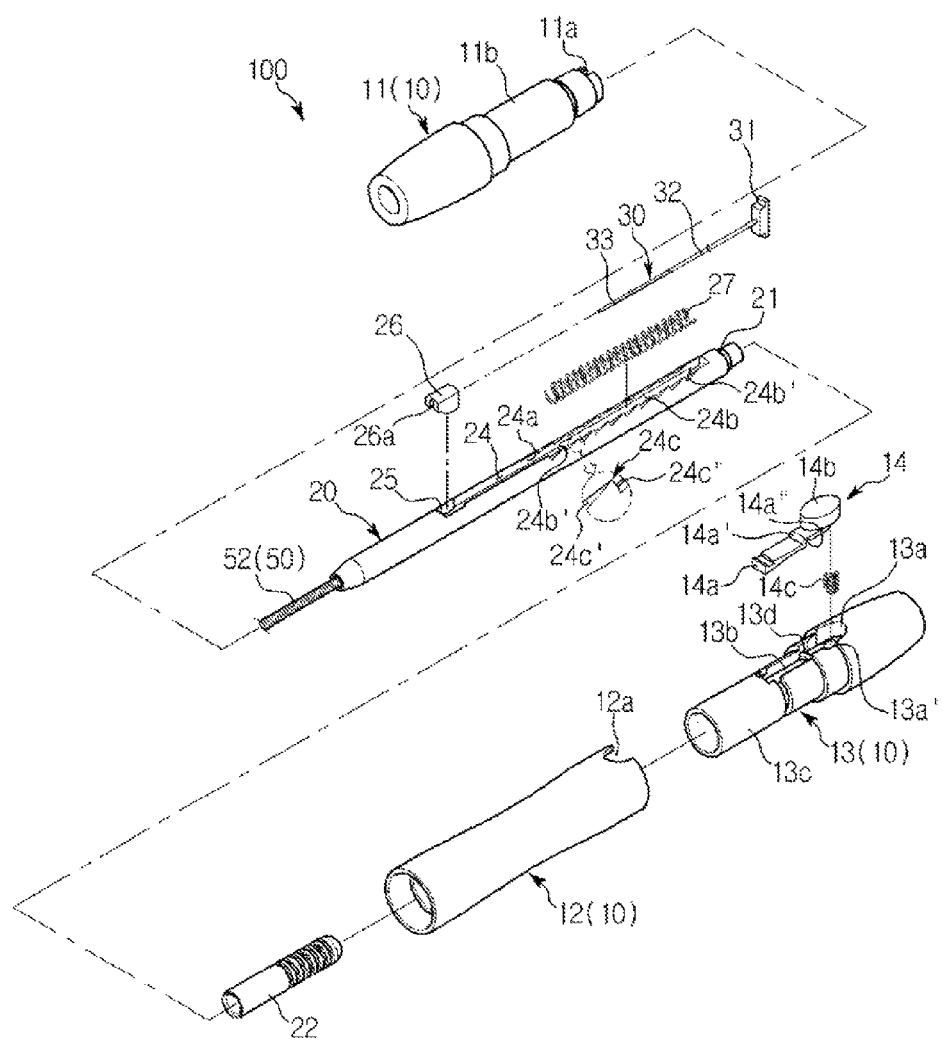
FIG. 1 is an exploded perspective view showing an apparatus of a transluminal procedure according to the present invention.

<Description of the Reference Numerals in the Drawings>

| | |
|---|---|
| 10: case | 10a: button space |
| 11: front case part | 11a: locking groove |
| 12: central case part | 12a: button hole |
| 12a': hinge portion | 13: rear case part |
| 13a: button groove | |
| 13a': second elastic body groove | |
| 13b: through-hole | 13c: fastening end |
| 14: locking member | 14a: locking end |
| 14a': vertical portion | 14a'''': hinge groove |
| 14b: button | |
| 14b': first elastic member groove | |
| 20: operation member | 21: body pipe |
| 22: cap | 23a: wire hole |
| 24: cut portion | 24a: inner side |
| 24b: guide groove | 24b': support end |
| 24c: locking step groove | 24c': inclined surface |
| 24c'''' vertical surface | 25: seat |
| 26: stopper | 26a: slit |
| 27: elastic member | 30: inner wire |
| 31: locking block | 32: wire |
| 33: plate-shaped wire | 40: variable portion |
| 50: outer tube | 51: front tube tip |
| 52: rear tube | 100: procedure apparatus |
| 200: plastic stent | 300: tongs |
| d: initial diameter | D: variable diameter |

BEST MODE

The present invention can fix a plastic stent by pressing, can simply move the plastic stent to adjust the position, and can automatically return the plastic stent, thereby allowing an operator to more conveniently perform a procedure in use.

MODE FOR INVENTION

Embodiments of the present invention will be described in detail with reference to the accompanying drawings.

Figure 2:
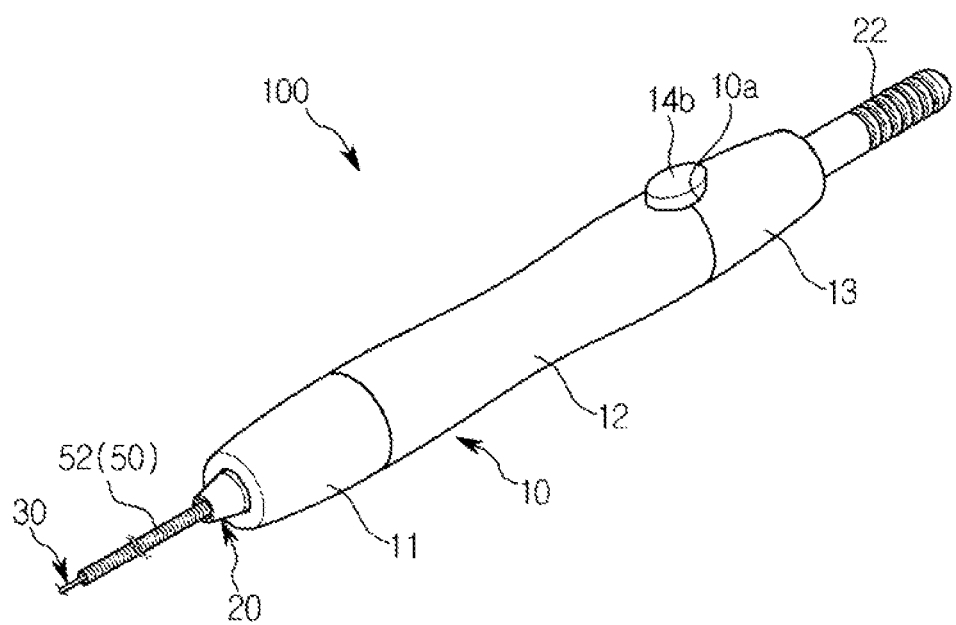
FIG. 2 is an assembled perspective view showing the apparatus of a transluminal procedure according to the present invention.
Figure 3:
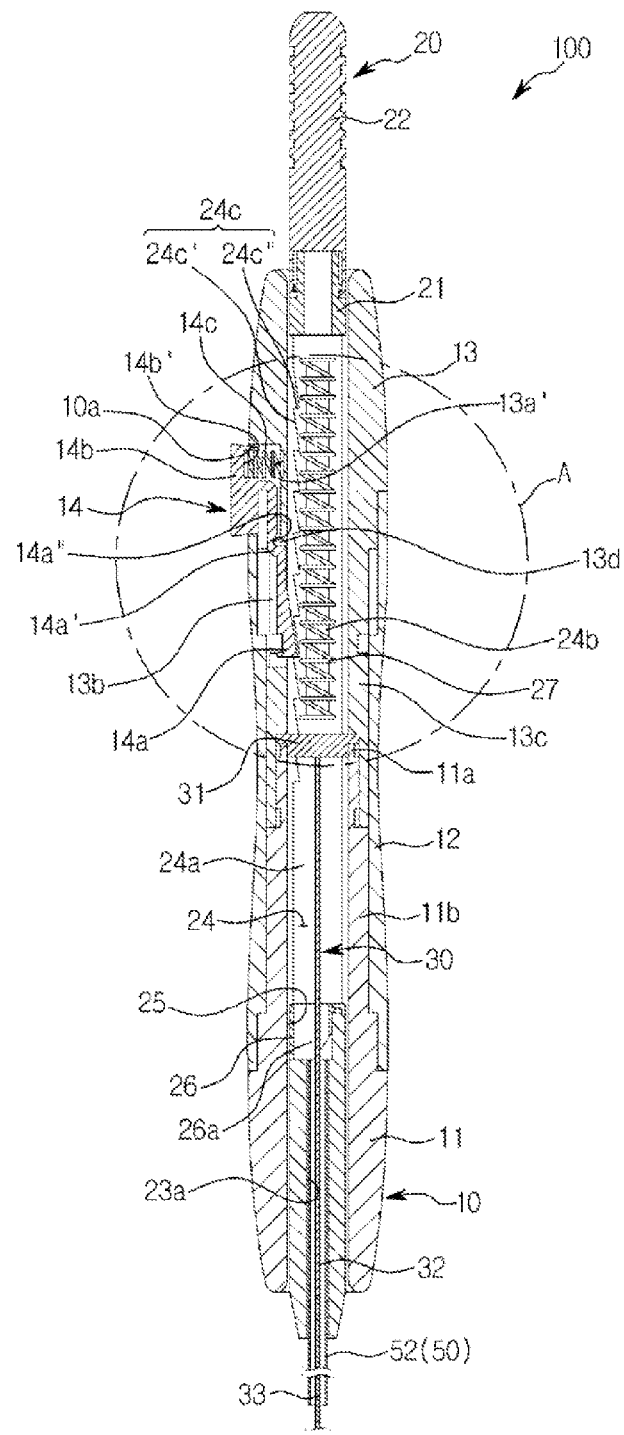
FIG. 3 is a cross-sectional view showing the apparatus of a transluminal procedure according to the present invention.
Figure 4:
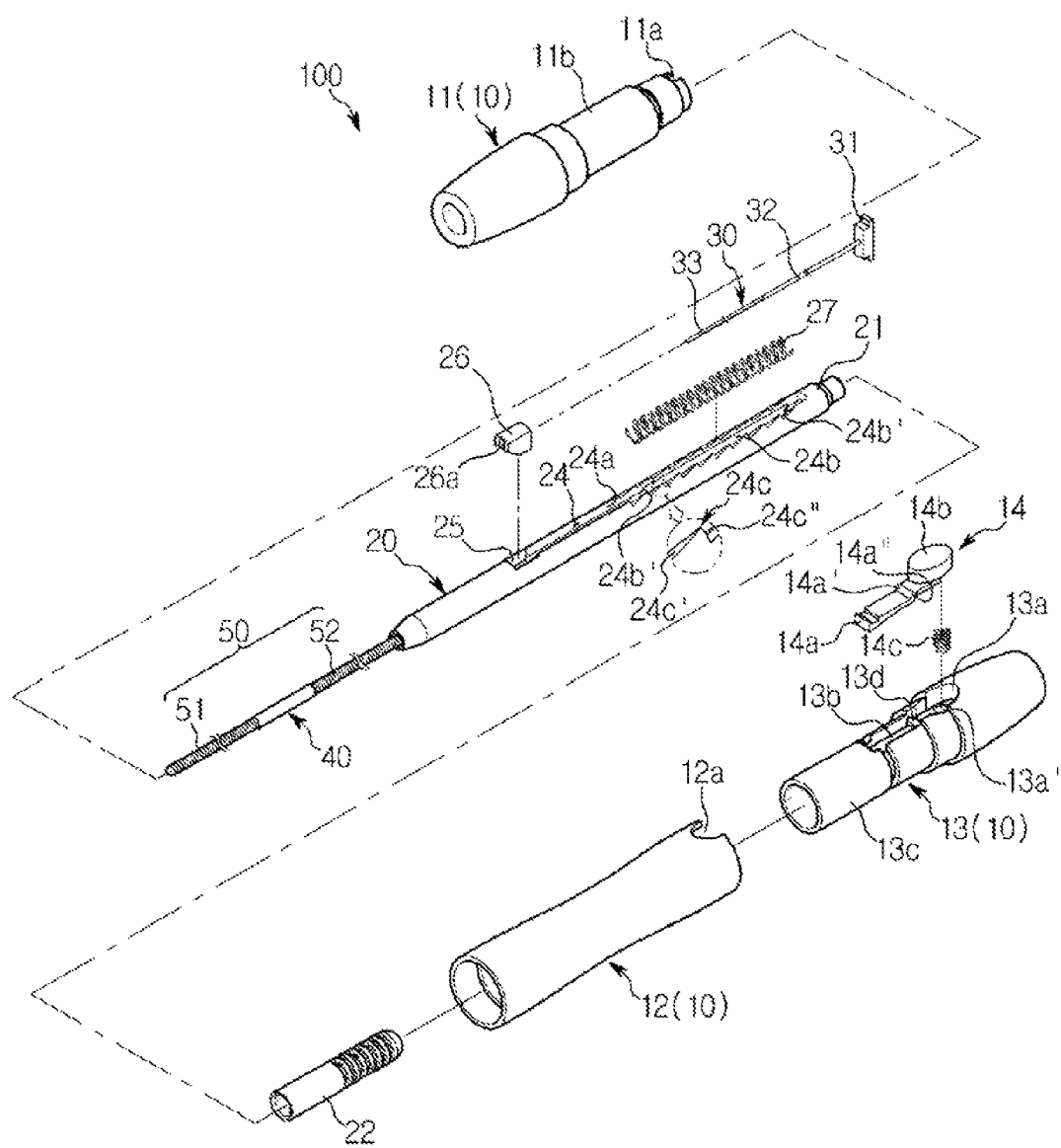
FIG. 4 is an exploded perspective view showing an apparatus for a transluminal procedure according to another embodiment.
Figure 5:
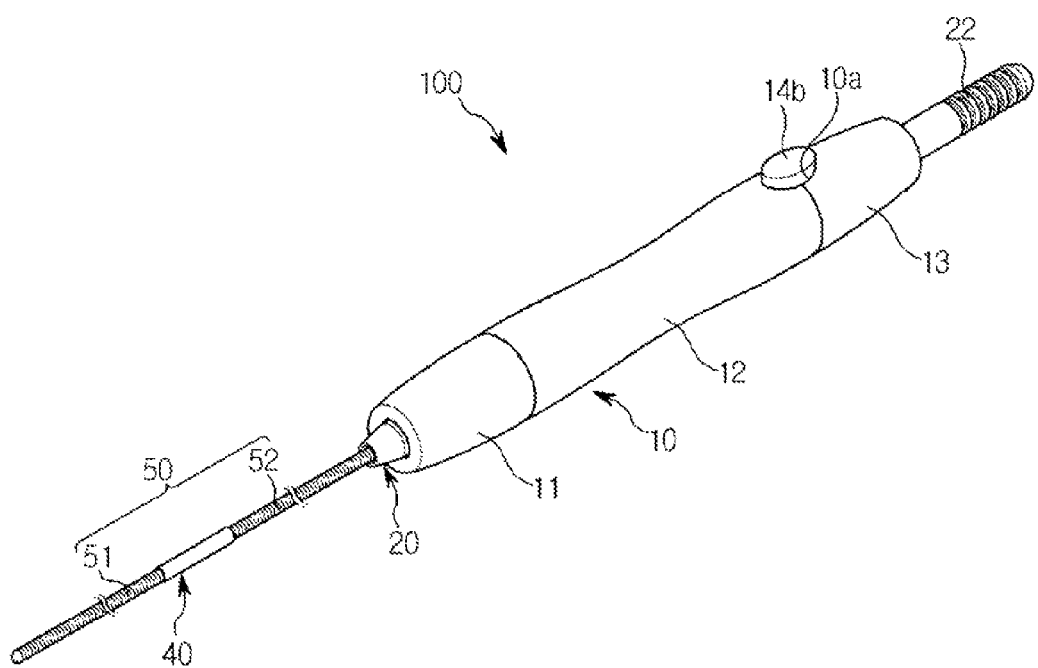
FIG. 5 is an assembled perspective view showing the apparatus for a transluminal procedure according to another embodiment.
Figure 6:
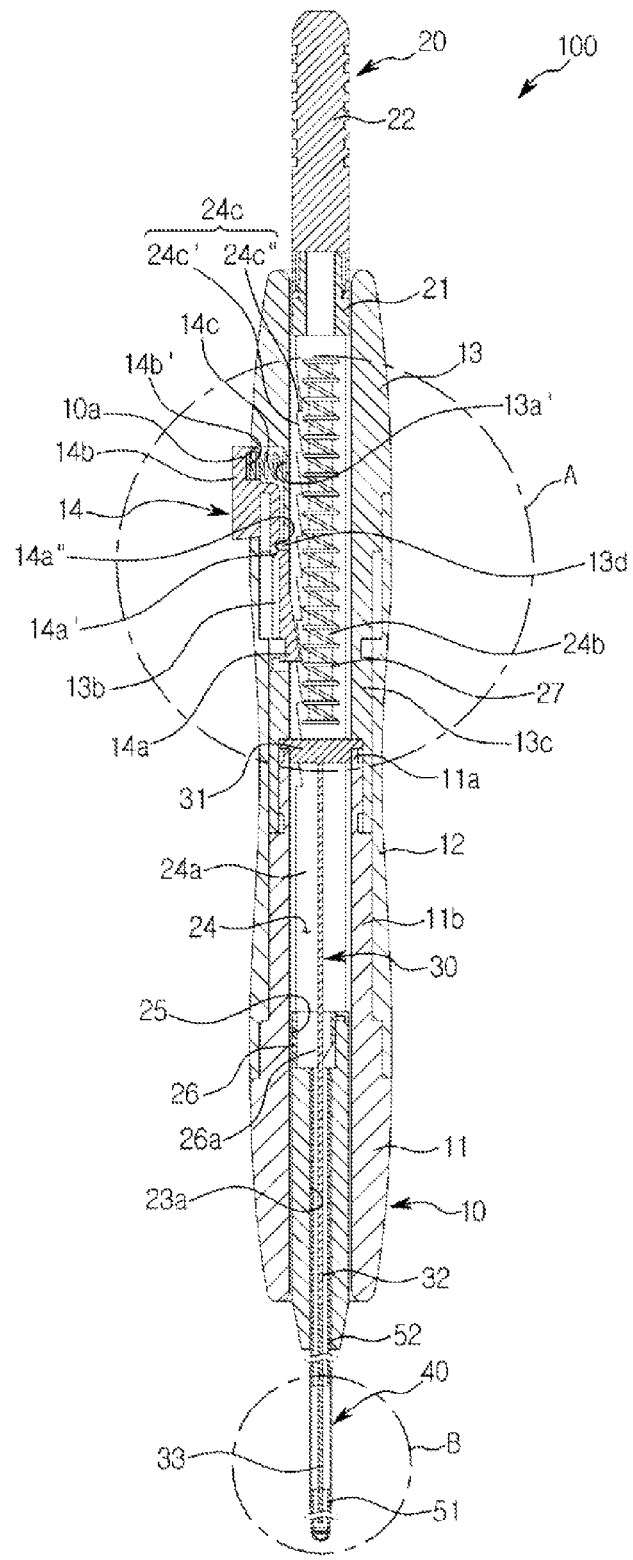
FIG. 6 is a cross-sectional view showing the apparatus for a transluminal procedure according to another embodiment.
Figure 7:
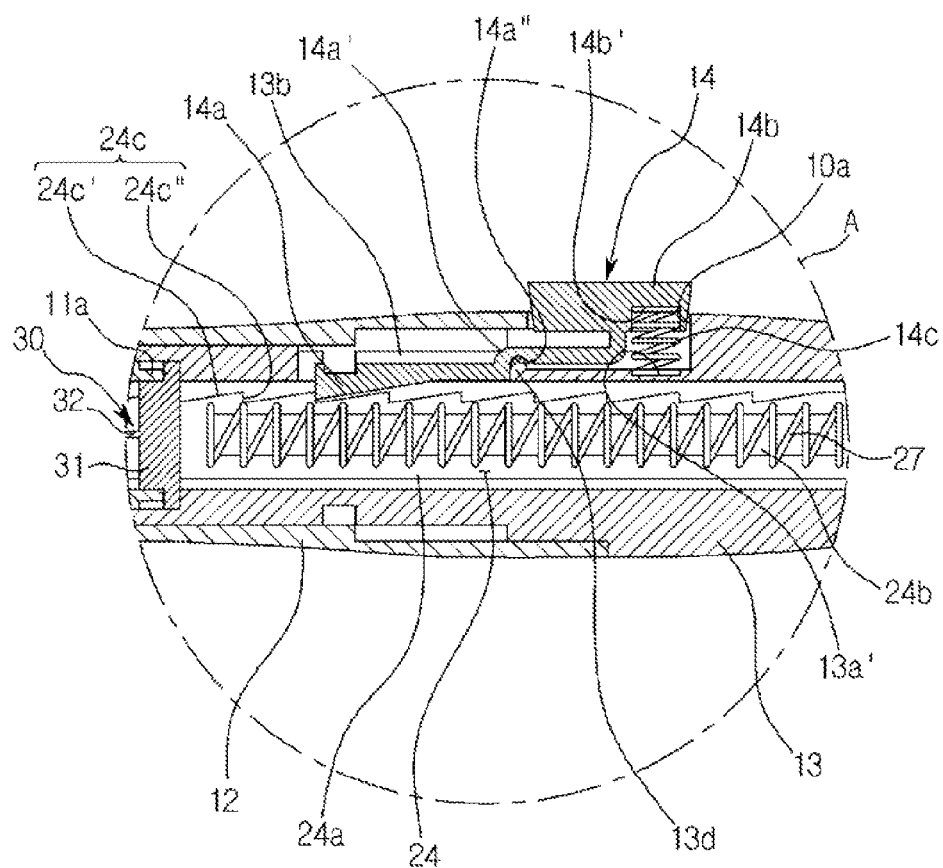
FIG. 7 is an enlarged view of the portion 'A' in FIGS. 3 and 6.
Figure 8A:
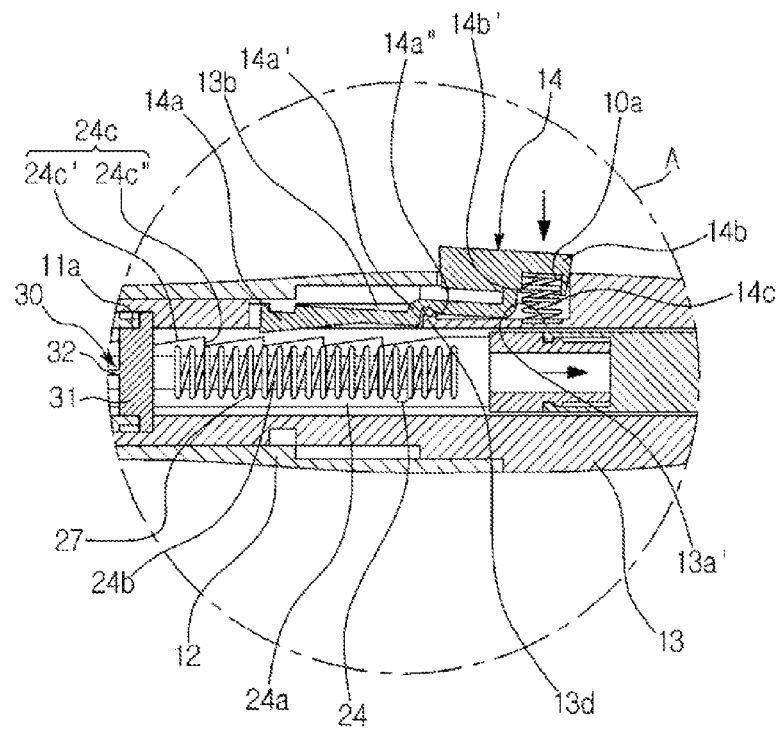
FIG. 8A is an enlarged view showing the operation of returning while an operation member is unlocked by operating a button.
Figure 8B:
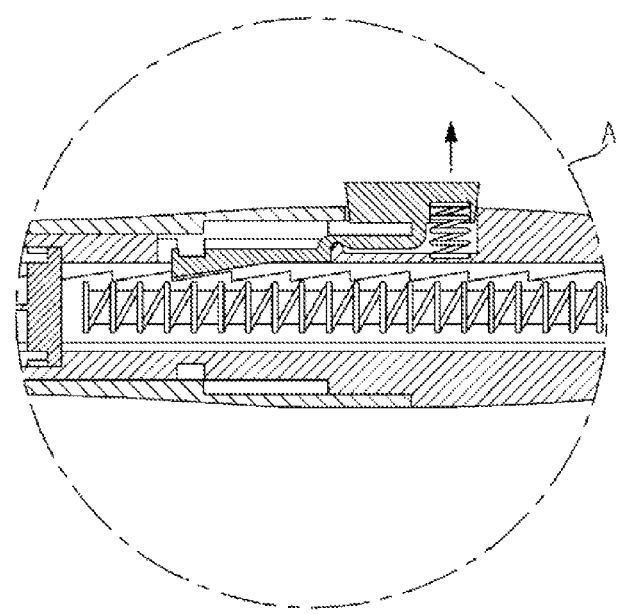
FIG. 8B is an enlarged view showing the operation of returning of the button.

An apparatus for a transluminal procedure of the present invention configures a procedure apparatus 100A that includes a case 10, an operation member 20 moving up/down in the case 10, an inner wire 30 inserted in the operation member and locked to the case 10, and an outer tube 50 fitted on the inner wire 30 and having a variable portion 40, as shown in FIGS. 1 to 3, and a procedure apparatus 100b having a configuration the same as the procedure apparatus 100A, but being disposed at a front tube tip 51 and a rear tube 52 of the outer tube 50 and changing the diameter of the variable portion 40 when the inner wire 30 is pulled and released, as shown in FIGS. 4 to 6.

As shown in FIGS. 1 to 8B, common features of the procedure apparatuses 100A and 100B will be described hereafter.

First, the case 10 of the procedure apparatuses 100A and 100B is formed in the shape of a tube and composed of a front case part 11, a central case part 12, and a rear case part 13.

In this configuration, the front case part 11 is fitted on the front portion of the operation member 20 and has a locking groove 11a at the rear end to which an end of the inner wire 30 is locked.

That is, the front case part 11 has a coupling portion 11b at one end on which the central case part 12 is fitted and a pair of locking grooves 11a are formed opposite each other at the end of a locking groove end 11c integrally extending from the coupling portion 11b.

Further, the central case part 12 is fitted on the operation member 20 and combined with the front case part 11 and has a button hole 12a at the rear end.

That is, the central case part 12 is formed in the shape of a pipe that is recessed at the middle portion for an operator of the front case part 11 to easily hold and of which both ends are larger in diameter, the opposite side to the button hole 12a is coupled to the front case part 11, and the end where the button hole 12a is formed, is coupled is coupled to the rear case part 13.

And, the rear case part 13 is fitted on the operation member 20 and coupled to the central case part 12 and a through-hole 13b is formed at a coupling portion 13c extending forward from a button groove 13a being in contact with the button hole 12a at the center.

A locking member 14 having a button 14b protruding rearward from a locking end 14a that comes in contact with the operation member 20 through the through-hole 13b is disposed, in the rear case part 13.

In this configuration, the locking member 14 has a step-shaped longitudinal cross-section, in which the locking end 14a is disposed at a lower portion, and the button 14b is disposed, at an upper portion. The locking end 14a and the button 14b are integrally connected with a vertical portion 14a' and a hinge portion 13d formed at the end where the button hole 12a and the button groove 13a of the upper case 10 are connected is inserted and rotated in a hinge groove 14a'' recessed under the vertical portion 14a'.

Further, the button 14b of the locking member 14 is supported by an elastic member 14c in the button groove 13a of the rear case part 13 to return and bring the locking end 14a in close contact with the an locking step groove 24c of the operation member 20, after being pressed.

And, the operation member 20 is a pipe-shaped operation member moving up/down in the case 10.

The operation member 20 includes a cap 22 that is attached/detached to/from the upper portion of a long body pipe 21.

Further, the body pipe 21 of the operation member 20 has a wire hole 23a formed through the center of the front portion.

Further, a cut portion 24 is formed longitudinally rearward in the operation member 20 to communicate with the wire hole 23a.

In this configuration, a plurality of locking step grooves 24c that is locked to the locking end 14a of the locking member 14 is formed along a cut line at a side of the cut portion 24.

That is, the locking groove 11a is configured such that the locking end 14a of the locking member 14 is locked to vertical surfaces 24c", which is formed behind inclined surfaces 24", while moving in contact with the inclined surfaces 23c' of the locking step groove 24c in a direction in which the operation member 20 is pressed.

In the cut portion 24, a seat 25 expanding in an area larger than the cut portion 24 is formed adjacent to the wire hole 23a through which the inner wire 30 passes.

A stopper 26 formed in a rectangular shape with a slit 26a is fitted in the seat 25 and the inner wire 30 passes through the slit 26a.

Guide grooves 24b are formed longitudinally formed to face each other on both inner sides of the cut portion 24, respectively, and the outer side of an elastic member 27 such as a spring inserted in the cut portion 24 is supported by the guide grooves 24b.

That is, support ends 24b' are formed at the upper and lower ends of the guide grooves 24b are closed in an arc shape to support the upper and lower ends of the elastic member 27.

The inner wire 30 is inserted in the operation member 20 and locked to the case 10.

A locking block 31 is integrally fixed at the end of the inner wire 30 that passes through the operation member 20 to be locked to the locking groove 11a of the front case part 11.

That is, the inner wire 30 passes through the wire hole 23a formed in the body pipe 21 of the operation member 20, passes through the slit 26a of the stopper 26 seated in the seat 25 formed in the cut portion 24 of the operation member 20, and is then integrally combined with the locking block 31 and locked to the locking groove 11a of the front case part 11.

Further, a plate-shaped wire 33 is integrally formed at the front end of a wire 32 at the rear end portion passing through the operation member 20 of the inner wire 30, the wire 32 is integrally combined with the locking block 31, and the plate-shaped wire 33 is formed ahead of it.

The plate-shaped wire 33 is inserted in the outer tube 50 to ensure a space where a guide wire can be inserted.

Further, the outer tube 50 covers the inner wire 30 and is fixed ahead of the operation member 20.

The outer tube 50 may be used as a single unit in accordance with the usage, but if necessary, it may be divided into the front tube tip 51 and the rear tube 52.

The procedure apparatuses 100A and 100B can be used for fixing the plastic stent 200, for functioning as forceps that removes a portion of a tissue using tongs, and for excising a tissue using a snare 400.

1. As shown in FIGS. 4 to 6, and FIGS. 9, 10A, and 10B, in both of the procedure apparatuses 100A and 100B, in order to fix and move the plastic stent 200, the outer tube 50 is composed of the front tube tip 51 and the rear tube 52, which are made of an elastic member such as rubber. The front tube tip 51 connected to the front of the variable portion 40, which contracts and increases in diameter when being pulled, is connected to the end of the plate-shaped wire 33 of the inner wire 30 and the rear tube 52 connected to the rear of the variable portion 40 is fixed to the front of the operation member 20.

That is, when the operation member 20 is pressed, the rear tube 52 moves with the operation member 20 with the case 10 and the inner wire 30 maintained at the original positions. Further, the variable portion 40 is pressed and increased in diameter, with the front tube tip 51 connected to the inner wire 30 maintained at the original position, and presses the inner side of the plastic stent 200, so the plastic stent 200 can be fixed.

Figure 11:
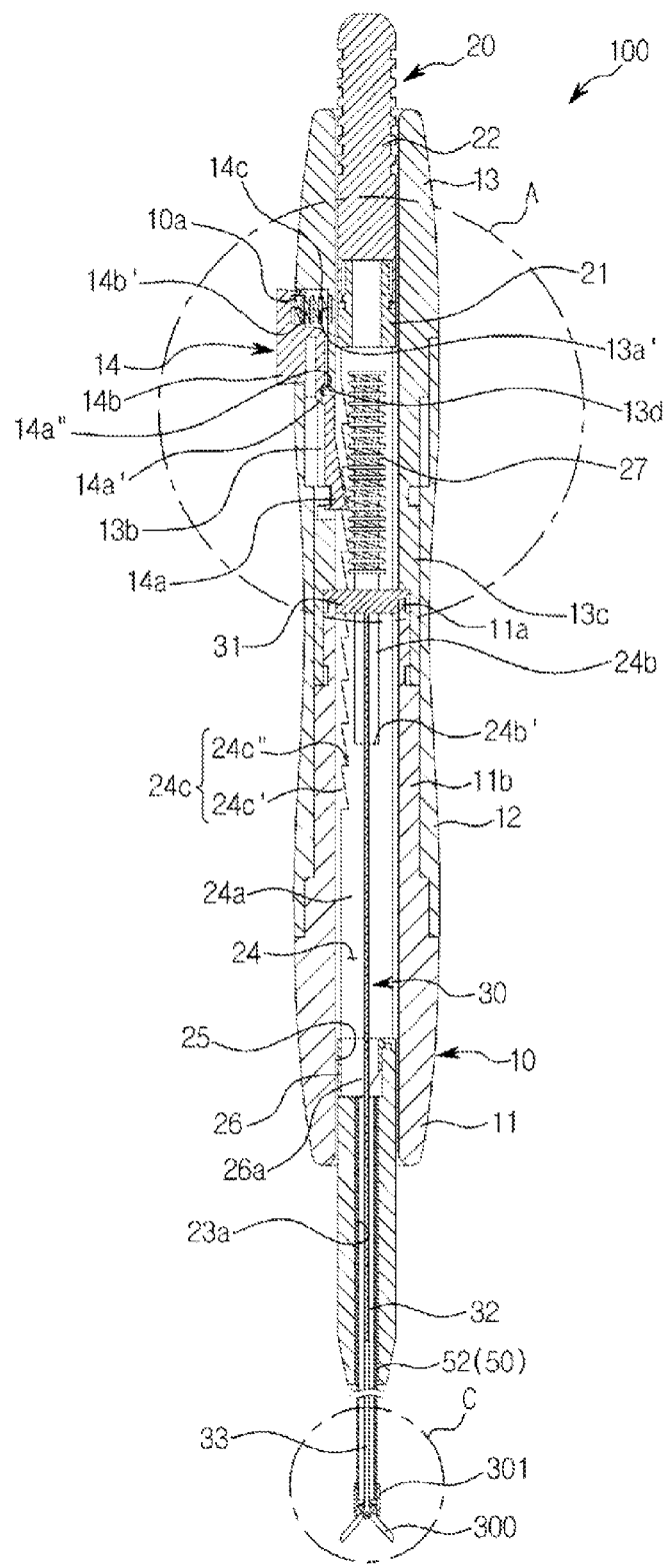
FIG. 11 is a cross-sectional view of a procedure apparatus for functioning as forceps.
Figure 12A:
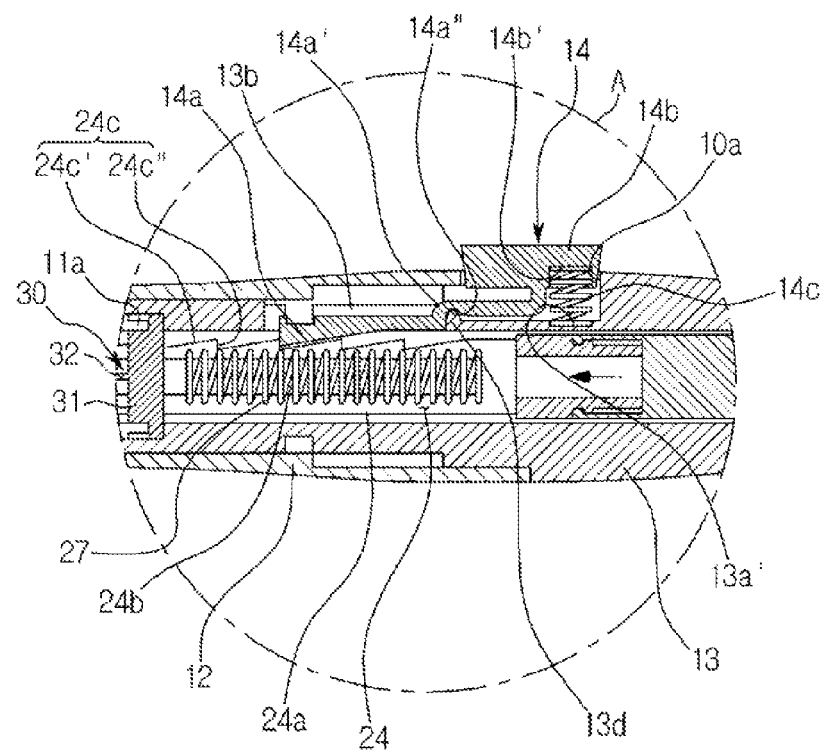
FIGS. 12A and 12B are operational views of the procedure apparatus for functioning as forceps.
Figure 12B:
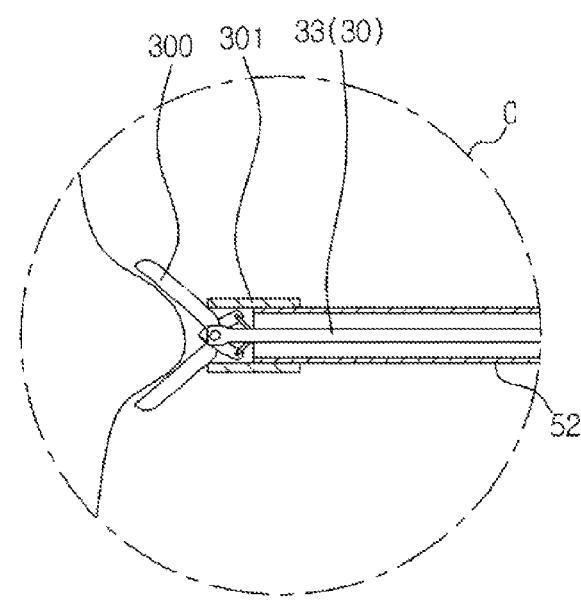

2. As shown in FIGS. 11, 12A, and 12B, according to the procedure apparatuses 100A and 100B that function as forceps for removing a portion of a tissue using tongs 300, the tongs 300 are connected to the end of the wire 32 of the inner wire 30 or the end of the plate-shaped wire 32 and a tongs body 301 having the tons 300 is connected to the front end of the rear tube 52 of the outer tube 50 to function as forceps.

That is, the tongs 300 are fastened to the tongs body 301 in a hinge type, so when the operation member 20 is pressed, the outer tube 50 moves with the operation member 20 with the case 10 and the inner wire 30 maintained at the original positions, and the tongs 300 close, whereas when the operation member 20 moves rearward, they are opened.

Figure 13:
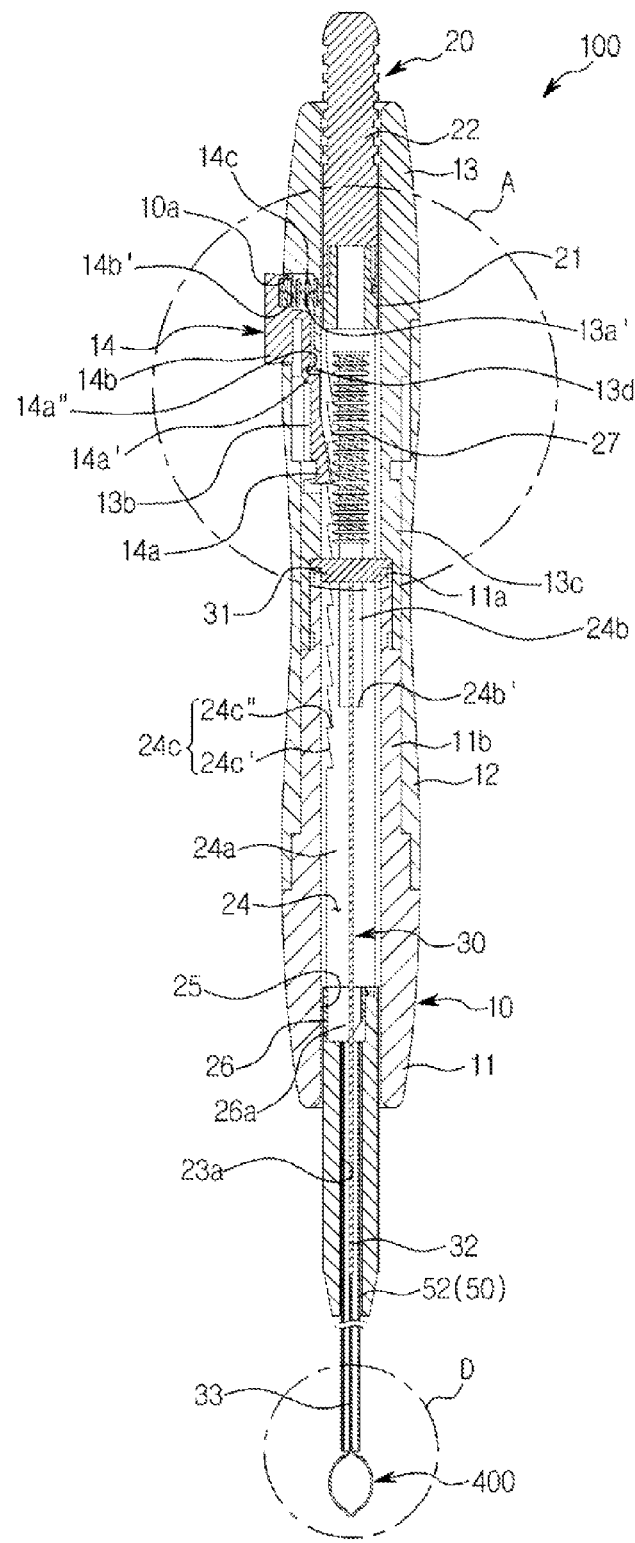
FIG. 13 is a cross-sectional view of a procedure apparatus for functioning as a snare.
Figure 14A:
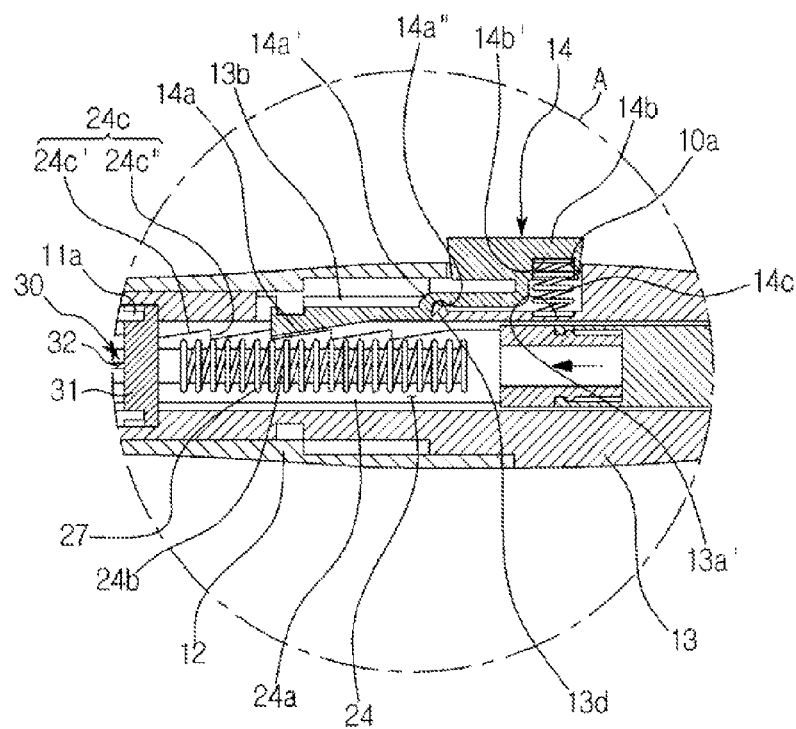
FIGS. 14A and 14B are operational views of the procedure apparatus for functioning as the snare.
Figure 14B:
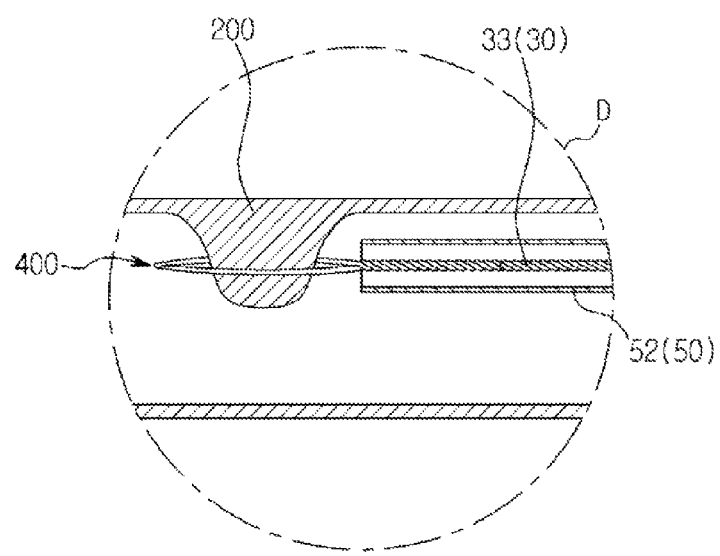

3. As shown in FIGS. 13, 14A, and 14B, according to the procedure apparatuses 100A and 100B for excising a tissue using a snare 400, the snare 400 is connected to the end of the wire 32 of the inner wire 30 or the end of the plate-shaped wire 33 to be moved into/out of the rear tube 52 of the outer tube 50.

That is, when the snare 400 presses the operation member 20 to the inner wire 30, the outer tube 50 moves with the operation member 20 with the case 10 and the inner wire 30 maintained at the original positions and the snare 40 is inserted, whereas when the operation member 20 moves rearward, the snare 400 is exposed.

The operation and effect of the present invention having the configuration are described hereafter.

As shown in FIGS. 1 to 8(b), the procedure apparatus 100A is connected by inserting the inner wire 30 of the outer tube 50.

Thereafter, the inner wire 30 of the outer tube 50 is inserted through the wire hole 23a of the operation member 20 and the outer tube 50 is fixed to the front end of the operation member 20.

Next, the inner wire 30 is inserted through the slit 26a of the stopper 26 in the seat 25 of the operation member 20 and then the locking block 31 is integrally combined with the end.

Next, the elastic member 27 is inserted through the cut portion 24 of the operation member 20 and then inserted into the guide groove 24b such that the outer side is supported and guided, the upper and lower ends of the elastic member 27 are combined to be supported by the support ends 24b' formed at the upper and lower ends of the guide groove 24b, and the cap 22 is coupled to the upper portion of the body pipe 21 of the operation member 20.

Thereafter, the front case part 11 is fitted on the front portion of the operation member 20 with the outer tube 50 therein, the locking block 31 of the inner wire 30 is inserted into the locking groove 11a of the front case part 11, and then the central case part 12 is coupled to the coupling end 11b of the front case part 11.

Next, a hinge end 13d of the rear case part 13 is fitted into a hinge groove 14a" of the locking member 14 such that the locking end 14a is inserted into the through-hole 13b, one end of the elastic member 14c is inserted into a first elastic member groove 14b' formed on the bottom of the button 14b and the other end is inserted into a second elastic groove 13a on the bottom of the button groove 13a so that the elastic member 14c elastically supports the button 14b to prevent the locking end 14a from being pushed into the space in the central case part 12, and the fastening end 13c of the rear case part 13 is inserted into the central case part 12.

Since the central case part 12 and the rear case part 13 are combined, the button groove 12a of the central case part 12 and the button groove 13a of the rear case part 13 communicate with each other, so a space into which the button 14b can be inserted when the button 14b of the locking member 14 is pressed is defined.

Thereafter, in order to use the procedure apparatus 100A, when an operator presses the upper end of the cap 22 of the operation member 20 exposed rearward out of the rear case part 13 with a thumb, with a hand holding the case 10, the operation member 20 is moved forward.

That is, as the operation member 20 is moved forward, the operation member 20 and the outer tube 50 are moved forward and the case 10 is moved rearward, so the inner wire 30 cannot move with the case 10 due to the blocking block 31 of the inner wire 30 locked to the locking groove 11a of the front case part 11.

While the operation member 20 is moved forward, the locking end 14a of the locking member 14 moves along the inclined surface 24c' of the locking groove 11a, and when the operation member 20 is stopped, the vertical portion 14a' is locked to the locking step groove 24c.

Since a plurality of locking step grooves 24c for locking the locking end 14a is formed and a movement distance can be adjusted, it is possible to simply adjust the rate of change in diameter of the variable portion 40.

The locking end 14a is moved in contact with the locking step grooves 24c of the operation member in the type of a latch by the elastic force of the elastic member 14c pushing up the button 14b of the locking member 14, so the locking end 14a can keep locked to the vertical portion 14a' and it is not easily unlocked even if an external force is applied.

Further, as the operation member 20 moves forward, the elastic member 27 is locked to the locking groove 11a of the front case part 11 and pressed by the locking block 31 moving rearward.

The elastic member 27 is compressed in the guide groove 24b of the operation member 20, so it is not separated from the cut portion 24.

The procedure apparatuses 100A and 100B can be used for fixing the plastic stent 200, for functioning as forceps that removes a portion of a tissue using tongs, and for excising a tissue using a snare 400.

Figure 9:
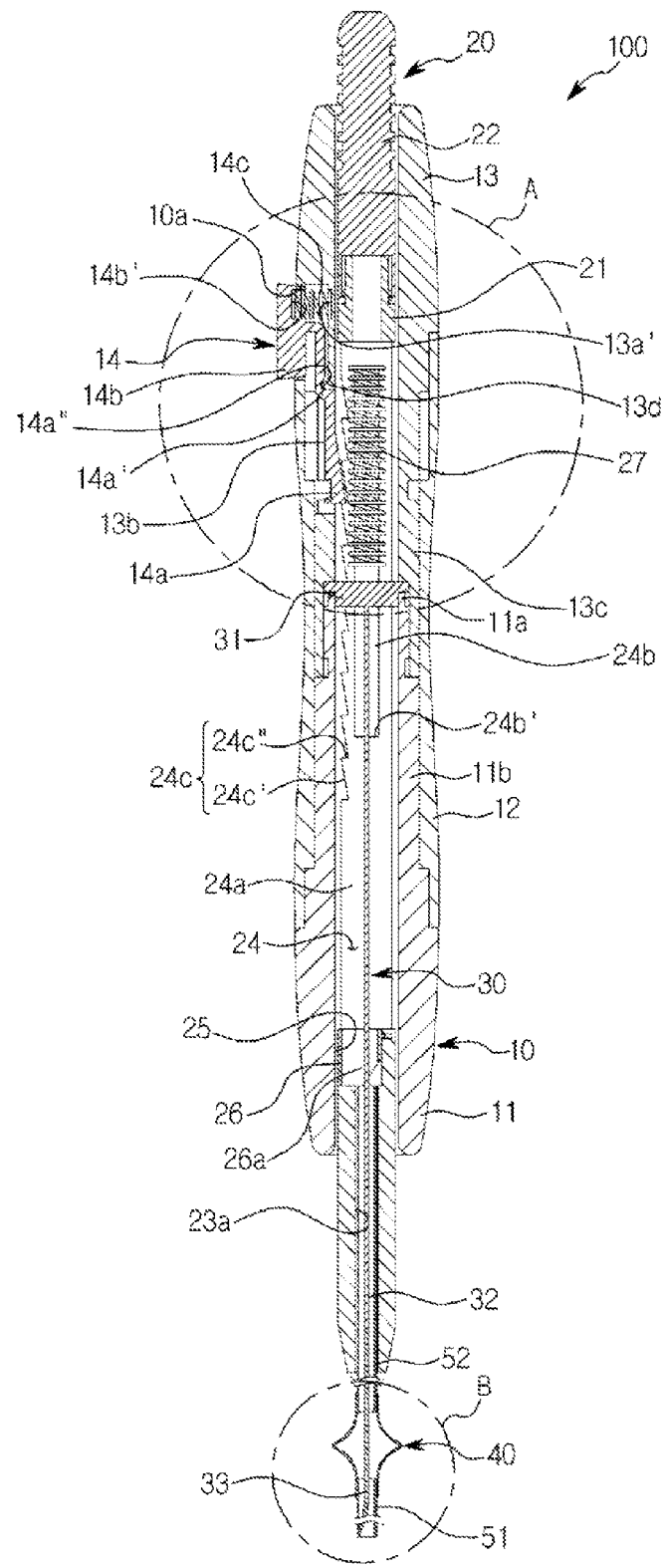
FIG. 9 is a cross-sectional view illustrating a procedure with a plastic stent.
Figure 10A:
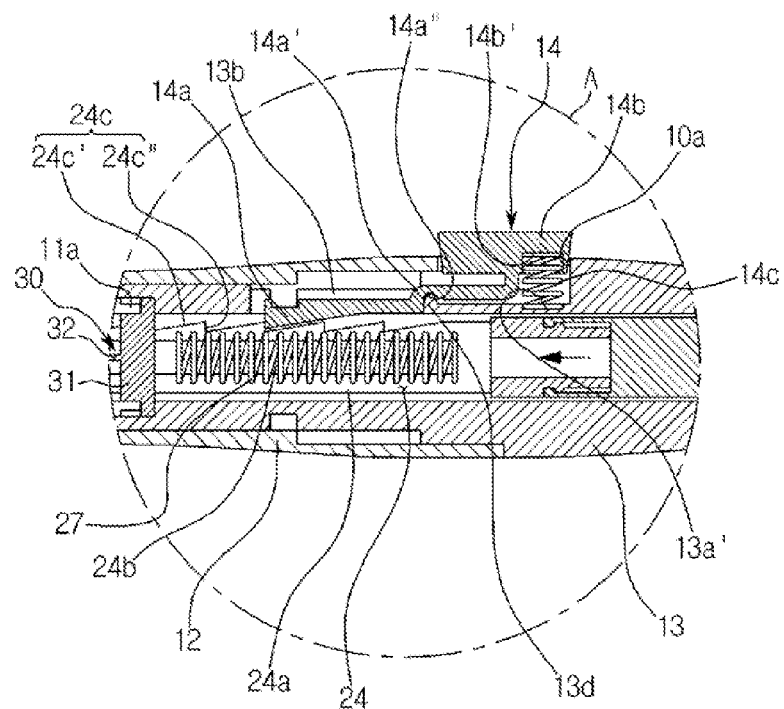
FIGS. 10A and 10B are operational views illustrating the procedure with the plastic stent.
Figure 10B:
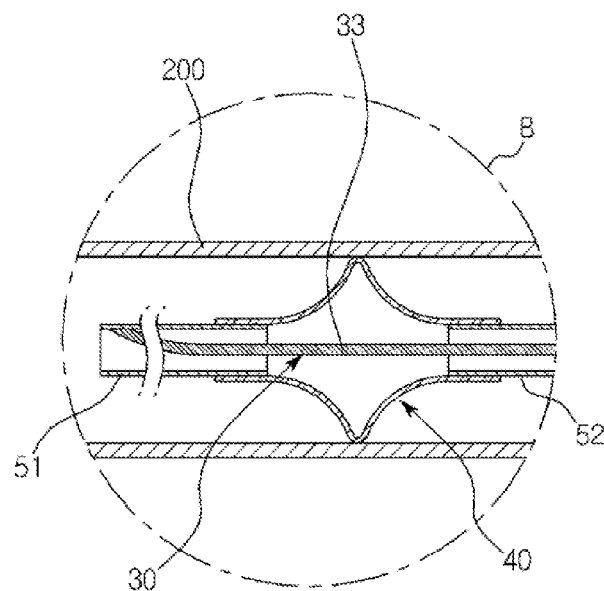

1. As shown in FIGS. 9, 10A, and 10B, in a process of fixing and moving the plastic stent 200, when the operation member 20 is moved forward, the front tube tip 51 connected to the plate-shaped wire 33 of the inner wire 30 is pulled with the case 10 and the rear tube 52 is moved forward with the operation member 20, so the variable portion 40 is pressed toward the longitudinal center and it expands at the center portion in the shape of a disc.

The variable portion 40 changes from the initial diameter d to a variable diameter D. When the plastic stent 200 is fixed and moved by the procedure apparatus 100, the variable portion 40 having the variable diameter D cornea in close contact with the inner side of the plastic stent 200 and transmits an expansion force to the plastic stent 200, so the plastic stent 200 can be fixed. Further, when the procedure apparatus 100A is moved forward/rearward with the plastic stent 200 fixed, the plastic stent 200 can be moved forward/rearward, so the position can foe easily adjusted.

In particular, using the procedure apparatus 100 can reduce the volume without covering the plastic stent 200 to fix or moving it and the plastic stent 200 can be simply moved along a lumen of a body without deforming.

On the other hand, with the plastic stent 200 fixed or moved by the procedure apparatus 100, when the button 14b of the locking member 14 in the rear case part 13 is pressed, the elastic member 14c is pressed, the locking end 14a is separated from the locking step groove 24c of the operation member 20, and the elastic member 27 extends by its elastic force.

The operation member 20 supported on the locking block 31 is quickly moved rearward to the initial position by the elastic force of the extending elastic member 27, so it can quickly prepare for the next operation.

2. As shown in FIGS. 11, 12A, and 12B, as for the procedure apparatuses 100A and 100B removing a portion of a tissue using the tongs 300 like forceps, when the operation member 200 is pressed, the outer tube 50 moves with the operation member 20 with the case 10 and the inner wire 30 maintained at the original positions and the tongs 300 close, but when the locking member 14 is unlocked and the operation member 20 moves rearward, the tongs 300 open and a tissue to be excised is inserted between the tongs 300. Thereafter, the tongs 300 nip and excise the tissue by pressing the operation member 200.

3. As shown in FIGS. 13, 14A, and 14B, as for the procedure apparatuses 100A and 100B for excising a tissue using the snare, when the operation member 20 is pressed, the inner wire 30 moves with the operation member 20 with the case 10 maintained at the original position and the snare 400 is inserted. In contrast, when the locking member 14 is unlocked and the operation member 20 moves rearward, the snare 400 comes out, in which when the operation member 20 is pressed with the snare 400 moved to surround a tissue to remove such as a polyp, the snare 400 is pulled, into the outer tube 50 and removes the polyp.

Although preferable embodiments of the present invention were described above with reference to the drawings, they are not limited thereto and may be changed and modified by those skilled in the art without departing from the scope of the present invention.

The invention claimed is:

1. An apparatus for a transluminal procedure, wherein a case is composed of a front case part formed in the shape of a pipe and having a locking groove at a rear end of the front case, a central case part combined with the front case part and having a button hole at a rear end of the central part, and a rear case part combined with the central case part and having a through-hole and a button groove being in contact with the button hole to receive a button, the button protrudes rearward from a locking end inserted in the through-hole, the button is supported by an elastic member disposed in the button groove of the rear case part, returns after being pressed, and constitutes a locking member having the locking end, an operation member is formed in the shape of a pipe and moving up and down in the case, an inner wire is inserted in the operation member and locked to the case, and an outer tube is fitted on the inner wire and fixed to a front end of the operation member.

2. The apparatus for a transluminal procedure of claim 1, wherein the operation member includes a cap attached and detached to and from an upper portion of a long body pipe.

3. The apparatus for a transluminal procedure of claim 2, wherein the long body pipe of the operation member has a wire hole formed through a center of a front portion, a cut portion is formed longitudinally rearward in the operation member to communicate with the wire hole, and a plurality of locking step grooves that is locked to the locking end of the locking member is formed along a cut line at a side of the cut portion.

4. The apparatus for a transluminal procedure of claim 3, wherein a seat expanding in an area larger than the cut portion is formed adjacent to the wire hole through which the inner wire passes in the cut portion, and a stopper formed in a rectangular shape with a slit is fitted in the seat.

5. The apparatus for a transluminal procedure of claim 4, wherein a plurality of guide grooves are formed longitudinally formed to face each other on both inner sides, respectively, of the cut portion.

6. The apparatus for a transluminal procedure of claim 5, wherein an outer side of an elastic member including a spring inserted in the cut portion is supported by the guide grooves.

7. The apparatus for a transluminal procedure of claim 1, wherein a locking portion is integrally fixed at an end of the inner wire that passes through the operation member to be locked to the locking groove of the front case part.

8. The apparatus for a transluminal procedure of claim 7, wherein a rear portion of the inner wire passing through the operation member is a wire integrally combined with a locking block, and a plate-shaped wire is integrally formed a front end of the wire and connected with a front tube tip.

9. The apparatus for a transluminal procedure of claim 1, wherein a plurality of tongs are connected to the inner wire and a tongs body where the plurality of tongs are disposed is connected to the outer tube to function as forceps.

10. The apparatus for a transluminal procedure of claim 1, wherein a snare is connected to the inner wire to move into and out of the outer tube.

11. The apparatus for a transluminal procedure of claim 1, wherein the outer tube is composed of a front tube tip and a rear tube, the front tube tip connected to a front of a variable portion, which is made of an elastic member and contracts and increases in diameter when being pulled, is connected with an end of the inner wire and the rear tube connected to a rear of the variable portion is fixed to a front end of the operation member.

12. An apparatus for a transluminal procedure, wherein a case is composed of a front case part formed in the shape of a pipe and having a locking groove at a rear end of the front case, a central case part combined with the front case part and having a button hole at a rear end of the central case, and a rear case part combined with the central case part and having a through-hole formed and a button groove being in contact with the button hole to receive a button, the button protrudes rearward from a locking end inserted in the through-hole, the button is supported by an elastic member disposed in the button groove of the rear case part, returns after being pressed, and constitutes a locking member having the locking end, an operation member is formed in the shape of a pipe and moves up and down in the case, an inner wire is inserted in the operation member and locked to the case, and an outer tube is fitted on the inner wire, in which a front tube tip connected to a front of a variable portion, which is made of an elastic member and contracts and increases in diameter when being pulled, is connected with an end of the inner wire and a rear tube connected to a rear of the variable portion is fixed to a front end of the operation member.

13. The apparatus for a transluminal procedure of claim 12, wherein the operation member includes a cap attached and detached to and from an upper portion of a long body pipe.

14. The apparatus for a transluminal procedure of claim 13, wherein the long body pipe of the operation member has a wire hole formed through a center of a front portion, a cut portion is formed longitudinally rearward in the operation member to communicate with the wire hole, and a plurality of locking step grooves that is locked to the locking end of the locking member is formed along a cut line at a side of the cut portion.

15. The apparatus for a transluminal procedure of claim 14, wherein a seat expanding in an area larger than the cut portion is formed adjacent to the wire hole through which the inner wire passes in the cut portion, and a stopper formed in a rectangular shape with a slit is fitted in the seat.

16. The apparatus for a transluminal procedure of claim 15, wherein a plurality of guide grooves are formed longitudinally formed to face each other on both inner sides, respectively, of the cut portion.

17. The apparatus for a transluminal procedure of claim 16, wherein an outer side of an elastic member including a spring inserted in the cut portion is supported by the guide grooves.

18. The apparatus for a transluminal procedure of claim 12, wherein a locking portion is integrally fixed at an end of the inner wire that passes through the operation member to be locked to the locking groove of the front case part.

19. The apparatus for a transluminal procedure of claim 12, wherein a rear portion of the inner wire passing through the operation member is a wire integrally combined with a locking block, and a plate-shaped wire is integrally formed a front end of the wire and connected with a front tube tip.

20. The apparatus for a transluminal procedure of claim 12, wherein a plurality of tongs are connected to the inner wire and a tongs body where the plurality of tongs are disposed is connected to the outer tube to function as forceps.

21. The apparatus for a transluminal procedure of claim 12, wherein a snare is connected to the inner wire to move into and out of the outer tube.

* * * * *